US00PP12738P2

(12) United States Plant Patent
Olesen et al.

(10) Patent No.: US PP12,738 P2
(45) Date of Patent: Jul. 2, 2002

(54) MINIATURE ROSE VARIETY 'POULHYR'

(76) Inventors: L. Pernille Olesen; Mogens N. Olesen, both of Hilllerødvejen 49, DK-3480 Fredensborg (DK)

( * ) Notice: Subject to any disclaimer, the term of this patent is extended or adjusted under 35 U.S.C. 154(b) by 13 days.

(21) Appl. No.: 09/607,328

(22) Filed: Jun. 30, 2000

(51) Int. Cl.[7] ..... A01H 5/00
(52) U.S. Cl. ..... Plt./121
(58) Field of Search ..... Plt./121

(56) References Cited

PUBLICATIONS

UPOV–ROM GTITM Computer Database, 2001/02, GTI Jouve Retrieval Software, citation for 'POULhyr'.

Community Plant Varity Office "Certificate on the Grant . . . " Jun. 7, 1999 6 pages. EU.

Community Plant Variety Office "Proposal For A Variety Denomination" 1 page Jan. 26, 1998 EU.

Community Plant Variety Office "Chapter IV: Decisions" Aug. 16, 1999 EU 2 pages.

Canadian Food Inspection Agency "Applications Accepted For Filing" Jan. 1999 Canada 1 page.

*Primary Examiner*—Bruce R. Campell
*Assistant Examiner*—Susan B. McCormick

(57) ABSTRACT

A new miniature rose plant which has abundant, pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of miniature rose plant which originated from a controlled crossing between 'POULhappy', U.S. Pat. No. 9,483 granted Mar. 26, 1996, and an unnamed seedling. The two parents were crossed and the resulting seeds were planted in a controlled environment. The new variety is named 'POULhyr'.

The new rose may be distinguished from its seed parent, 'POULhappy', by the following combination of characteristics:

1. 'POULhappy' has more flowers than 'POULhyr',
2. The flower color of 'POULhappy' is orange-red, while the flower color of 'POULhyr' is pink.

The new variety may be distinguished from its pollen parent, an unnamed seedling, created by the same inventors, by the following combination of characteristics:

1. The unnamed seedling has orange-red colored flowers, while 'POULhyr' is pink.
2. The unnamed seedling produces more flowers than 'POULhyr', however the growth is more sensitive to disease.

The objective of the hybridization of this rose variety for commercial greenhouse culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULhyr' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULhyr' was selected by the inventors as a single plant from the progeny of the hybridization in Spring, 1995.

Asexual reproduction of 'POULhyr' by cuttings and traditional budding was first done by L. Pernille and Mogens N. Olesen in Fredensborg, Denmark in July, 1995. This initial and other subsequent propagations conducted in controlled environments have demonstrated that the characteristics of 'POULhyr' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULhyr'. Specifically illustrated in SHEET 1:

1. Stem showing branching and the attachment of leaves, buds, and peduncles;
2. Flower bud, partially opened bud, and open bloom;
3. Flower petals, detached;
4. Sepals, receptacle, and pedicel;
5. Flowering stem as well as a bare stem exhibiting thorns;
6. Leaves.

DETAILED DESCRIPTION OF THE VARIETY

The following is a description of 'POULhyr', as observed in its growth in glasshouses in Half Moon Bay, Calif., in plants aged sixteen weeks. Color references are made using The Royal Horticultural Society (London, England) Colour Chart, 1995, except where common terms of color are used. For a comparison, several physical characteristics of the rose variety 'POULnye', a pink rose variety from the same inventors described and illustrated in U.S. Plant Pat. No. 9,483 and issued on Mar. 26, 2000 and .

CHART 1

| | 'POULhyr' | 'POULnye' |
|---|---|---|
| Petal color, upper surface. | Red Group 52B. | Red-Purple Group 62B. |
| Petal color, lower surface. | Red-Purple Group 58C. | Red-Purple group 62C. |
| Petal arrangement and petal count. | Imbricated. Very double. 40 to 45 petals. | Informal. Double. 30 to 40 petals. |

Parents: 'POULhappy'×Unnamed seedling.

Classification:

*Botanical.*—*Rosa hybrida.*

*Commercial.*—Miniature.

FLOWER AND FLOWER BUD

Blooming habit: Continuous.

Flower bud:

*Size.*—Upon opening, 18 mm–22 mm in length from base of receptacle to end of bud.

*Bud form.*—Globular to ovoid.

*Bud color.*—As sepals unfold, Red-Purple Group 58C. Red-Purple Group 58C at ¼ opening.

*Sepals.*—Length: 10 mm. Width: 5 mm. Coloration is Green Group 144A. Weak to moderate foliaceous appendages on three of the five sepals. Surfaces of sepals slightly pubescent. Stipitate glands present on margins of sepals.

*Receptacle.*—Surface: With small hairs. Shape: Urn-shaped. Size: Small. 4 mm (h)×5 mm (w). Color: Yellow-Green Group 144A.

*Peduncle.*—Surface: With limited numbers of fine hairs and stipitate glands. Length: 20 to 40 mm average length. Color: Yellow-Green Group 144A. Strength: Strong.

*Borne.*—Generally with 3 to 4 buds per flowering stem.

Flower bloom:

*Fragrance.*—Light.

*Duration.*—As a pot plant, flowers last from 3 to 5 days.

*Size.*—Small for a 10 cm pot rose. Average flower diameter is 35–40 mm when open.

*Form.*—Shape of flower when viewed from the side: Upon opening, upper part: Cupped. Upon opening, lower part: Flat. Open flower, upper part: Flattened convex. Open flower, lower part: Flat.

*Petalage.*—Average range: 40 to 45 petals under normal conditions with petaloids.

Color:

*Upon opening, petals.*—Outermost petals: Upper Surface: Red Group 52B in middle and marginal zones; White Group 155C in basal zone. Reverse Side: Red-Purple Group 58C. Innermost petals: Upper Surface: Red Group 52 A and B in middle and marginal zones; White Group 155C in basal zone. Reverse Side: Red-Purple Group 58 B and C in middle and marginal zones; White Group 155C in basal zone.

*Upon opening, basal petal spots.*—Outer Side: Yellow Group 4D. Inner Side: Yellow Group 4D.

*After opening, petals.*—Outermost petals: Upper Surface: Red Group 52B in middle and marginal zones; White Group 155C in basal zone. Reverse Side: Red-Purple Group 58 C and D in middle and marginal zones; White Group 155C in basal zone. Innermost petals: Upper Surface: Red Group 52B in middle and marginal zones; White Group 155C in basal zone. Reverse Side: Red-Purple Group 58 C and D in middle and marginal zones; White Group 155C in basal zone.

*Upon opening, basal petal spots.*—Outer Side: Yellow Group 4D. Inner Side: Yellow Group 4D.

General tonality: On open flower Red Group 52A. No change in the general tonality at the end of the $4^{th}$ to $5^{th}$ day. Afterwards, general tonality is Red Group 52 B and C.

Petals:

*Petal reflex.*—Innermost petals display little to no reflex. Outermost petals are slightly reflexed.

*Petal margin.*—Point in center of margin.

*Shape.*—Deltoid.

*Petaloids.*—Quantity: 5 to 10.

*Thickness.*—Thick.

*Arrangement.*—Imbricated.

Reproductive organs:

*Pollen.*—Color: Yellow-Orange Group 14C. Quantity: Scant.

*Anthers.*—Size: Medium. Color: Yellow-Orange Group 14C.

*Filaments.*—Color: Yellow-Green Group 149C. Length: 4 to 5 mm.

*Stigmas.*—Slightly superior in location to anthers. Color: Green-White Group 157A.

*Styles.*—Color: Green-White Group 157A. Length: 6 to 7 mm.

*Hips.*—None observed.

PLANT

Plant growth: Vigorous and bushy. When grown as a 10 cm pot plant, the average height of the plant is 18 to 22 cm and the average width is 20 to 22 cm.

Stems:

*Color.*—Young wood: Green Group 146B. Older wood: Green Group 146B.

*Thorns.*—Incidence: Few. Size: Average length: 2 mm–3 mm. Color: Greyed-Green Group 193C. Shape: Linear.

*Surface.*—Young wood: Smooth. Older wood: Smooth.

*Length.*—Under typical greenhouse production conditions, stem length is 25 to 30 cm. Internode length varies from 8 to 10 cm.

Plant foliage: Normal number of leaflets on normal leaves in middle of the stem: 5 leaflets.

*Leaf size.*—65 to 80 mm (l)×45 to 50 mm (w).

*Abundance.*—*Average.*

*Color.*—*Upper Leaf Surface: Green Group* 137A. Lower Leaf Surface: Green Group 138B. Anthocyanin intonation: Location: Limited anthocyanin intonation on leaflet margins, underside of leaflets, and stipules. Color: Greyed-Red Group 179B.

Plant leaves and leaflets:

*Stipules.*—Size: 8 to 10 mm. Color: Green Group 137B. On plants grown in high light conditions, juvenile stipules with intonations of Greyed-Red Group 179B.

Presence of stipitate glands: Limited numbers on margins.

*Petiole.*—Length: 12 to 16 mm. Color: Green Group 137B. Underneath: Limited stipitate glands and small prickles.

*Rachis.*—Color: Green Group 137B. Underneath: Limited stipitate glands and small prickles. Margins: With stipitate glands.

*Leaflet.*—Edge: Finely serrated. Shape: Ovate. Other: Matte finish. On plants grwon in high light conditions, undersides and margins of juvenile leaflets with intonations of Greyed-Red Group 179B.

Disease resistance: Average resistance to mildew, black spot, and Botrytis under normal growing conditions in Half Moon Bay, Calif.

Cold hardiness: 'POULhyr' has been found to be resistant to damage from cold, heat and drought damage in USDA Zone 7.

We claim:

1. A new and distinct variety of rose plant of the miniature class, substantially as herein illustrated and described as a distinct and novel rose variety due to its abundant, pink flowers, vigorous and bushy growth, year round flowering under glasshouse conditions, suitability for production from softwood cuttings in pots, and durable flowers and foliage which make the variety suitable for distribution in the floral industry.

* * * * *

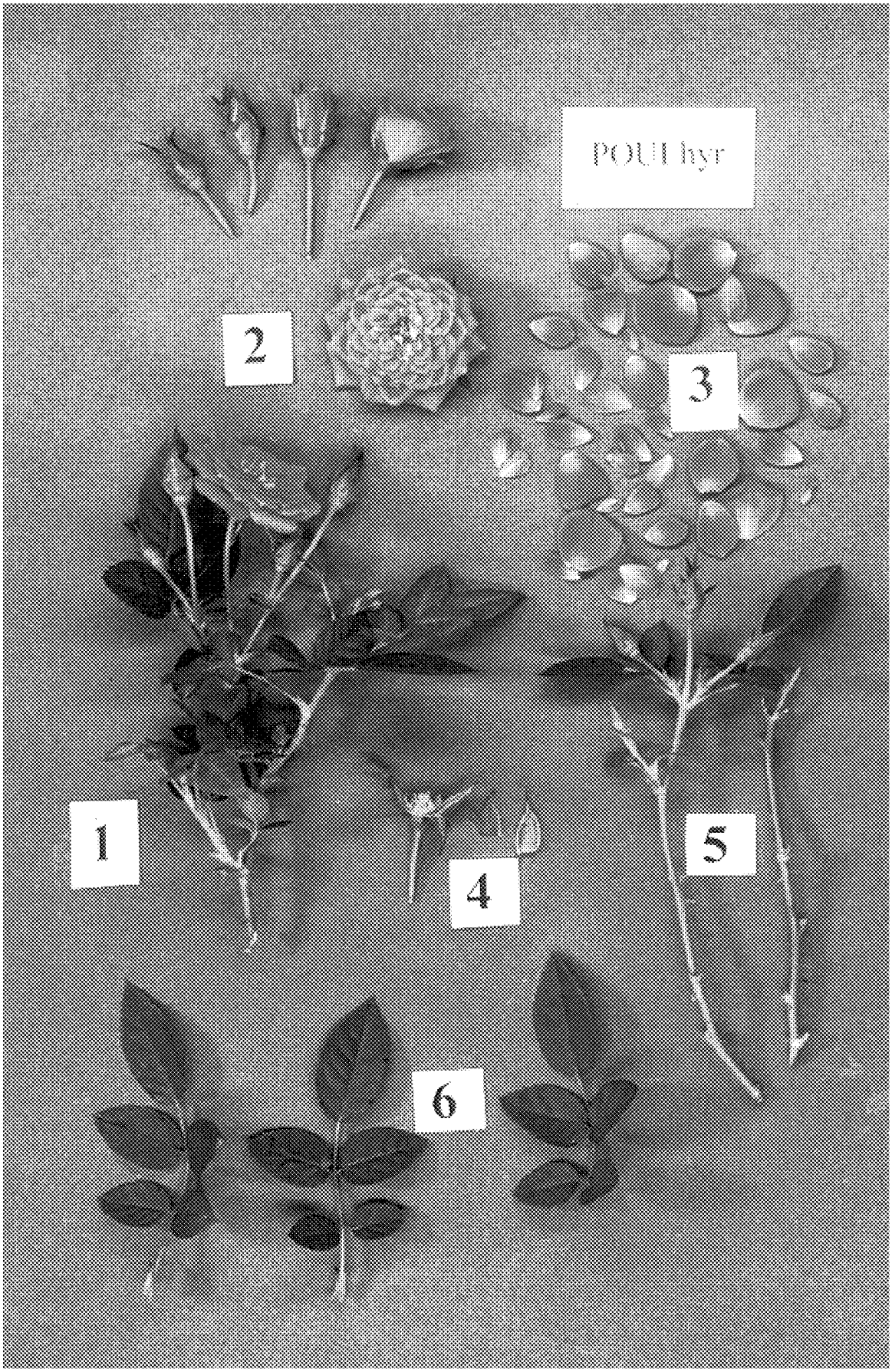
POUI hyr
2
3
1
4
5
6